Figure 1:
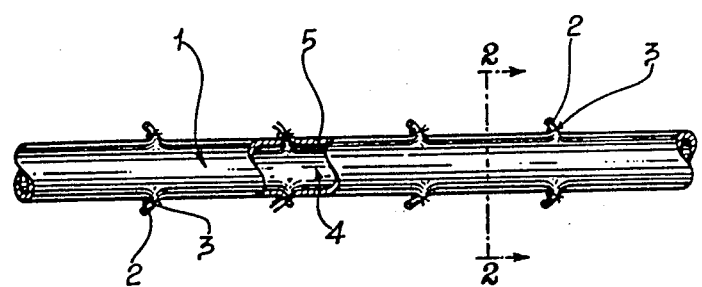

United States Patent [19]

Vrandecic Pedero

[11] Patent Number: 4,671,797
[45] Date of Patent: Jun. 9, 1987

[54] HETEROLOGOUS ARTERIAL BIOGRAFT AND BIOLOGICAL MATERIAL TREATING PROCESS

[76] Inventor: Mario O. Vrandecic Pedero, Rue Prof. Antonio Aleixo No. 307, Belo Horizonte, Minas Gerais, Brazil

[21] Appl. No.: 778,122

[22] Filed: Sep. 20, 1985

[30] Foreign Application Priority Data

Sep. 21, 1984 [BR] Brazil .......................... PI 8404772[U]

[51] Int. Cl.⁴ ................................................ A61F 2/06
[52] U.S. Cl. ...................................................... 623/1
[58] Field of Search .......................... 623/1, 12, 66 B; 128/334 R; 8/94.11

[56] References Cited

U.S. PATENT DOCUMENTS

| 3,570,013 | 3/1971 | Blumen | 623/1 |
| 3,588,920 | 9/1969 | Wesolowski | 623/1 |
| 4,098,571 | 7/1978 | Miyata | 623/1 |

Primary Examiner—Gregory E. McNeill
Attorney, Agent, or Firm—Ladas & Parry

[57] ABSTRACT

This invention concerns a heterologous arterial biograft comprehending a heterologous biological material-made arterial duct, having its branches bound together (through micro technique) and keeping to a great extent its natural characteristics after submitted to a complete curing by a diabasic acid aldehyde aqueous balanced solution. The arterial duct shall preferably be a swine's or bovine's internal mammary artery.

7 Claims, 2 Drawing Figures

U.S. Patent  Jun. 9, 1987  4,671,797

HETEROLOGOUS ARTERIAL BIOGRAFT AND BIOLOGICAL MATERIAL TREATING PROCESS

This invention generally concerns a biological graft and more particularly concerns the replacement of arteries and human veins by a heterologous arterial biological material-made tubular graft.

Two types of arterial grafts are currently known:
(a) biological grafts, comprehending: (i) saphena vein autografts and (ii) umbilical cord homografts and
(b) bovine carotid artery heterografts.

The saphena vein autograft is mostly used as its elastic structure, inner surface and inner diameter proportion remain unaltered. Saphena veins however not always can be used. The umbilical cord vein homograft is thicker and not so elastic and so is the bovine carotid artery heterograft.

We further have:
(c) DACRON (DU PONT's trademark) tubular prothetic and similar grafts, the patency of which (permeability or disobstruction condition) is highly inconvenient on account of inner smaller diameters.

To date, there is no arterial graft that may meet the requisites of patency, proportion, flexibility, etc., with the exception of the saphena vein autograft that not always is the most suitable solution (varices) nor always can be used by reason of saphenectomies formerly performed on the patient. Thus, a synthetic or heterologous arterial biograft to compensate for such deficiencies is needed, particularly a graft having a caliber comparable to the medium and small-sized caliber human arteries as a replacement for coronary arteries, should arterial autografts be not available.

This invention aims at overcoming the disadvantages of the above conventional technique, through a heterologous, arterial biological material tubular graft having characteristics of flow, patency, flexibility, inner wall surface homogeneity, inner diameter caliber and proportion to the wall thickness comparable to those of the receiving patient.

This invention also aims at covering the biological material treating process applicable to the preparation of the graft.

The detailed description below related to the attached drawings shall contribute towards making the invention known better:

FIG. 1: upper schematic diagram of the invented graft; and

Figure 2:
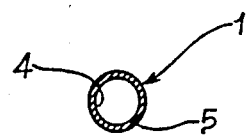

FIG. 2: cross section schematic diagram through the FIG. 1's 2—2 line.

As FIGS. 1 and 2 show, the arterial biograft comprehends a smooth arterial duct (1) without internal valves, made of a heterologous biological artery, the branches (2) of which are bound together (3). The preferred heterologous biological artery pursuant to this invention is an animal internal mammary artery, preferably swine's or bovine's depending on the desired arterial caliber. Typically, the artery treated by the below described process keeps a natural elasticity ranging from 40% to 60%; an inner wall (4) homogeneity ranging from 0.5 mm to 1,00 mm and an inner diameter proportion to the wall thickness kept within a 9:0.5 mm to 7:1.5 mm range.

The biological material treating process as contemplated by this invention comprehends the taking of an animal artery—preferably a swine or bovine internal mammary artery—followed by the immediate binding (through micro technique) of every arterial branch, the duct as thus treated to be left to complete curing in an aqueous diabasic acid (succinic or glutaric—the glutaric acid to be preferred) aldehyde balanced solution. The aldeheyde solution concentration range shall extend from 0.001% to 3% approximately. The solution of this invention shall preferably comprehend both monomeric and polymeric free anhydride glutaric aldehydes, so that the monomer-polimer unsaturated alpha and beta polimer-free ratio be 3:1. The solution is them tamponed with Mg group ions—preferably $Mg+S^-O_4$ ion—until a physiological pH (preferably above 7) is reached. This is a rather important feature for controlling the invention for it has been ascertained that, to keep the biological tissues duly preserved, the ionic power of the solution should be such that the existing ions—as spetrophotometrically proven—be kept between 230 Å and 300 Å approximately.

In addition, an ammoniated chlorined oxyde from an element—preferably iron or ruthenium—of the Periodic Table's group 8 meant to act as a biological tissue fixative is considered to specifically preserve the polysaccharide mucus and the proteoglycogen in the matrix and in the basal membrane, thus contributing to increasing the durability of the biological tissue. The invention concerns the application of an amount ranging from 0.02% to about 3% of the desired oxychlorate weight solution at a temperature higher than 10° C. but less than the degradation temperature of the solution components and the biological material is to be left in the solution to curing until a satisfactory histopathologically controlled curing of the material is obtained. It should be clear that any improvement may be made to the material provided, however, that no deviation from the original inventive concept as above described and as hereafter claimed occurs.

I claim:

1. Biological material treating process, characterized by the taking of an animal artery, followed by the immediate binding (through micro technique) of every arterial branch; treatment of the bound duct to complete curing in a diabasic acid (to be selected out of succinic and glutaric acids—the glutaric acid to be preferred) aqueous aldehyde balanced solution that shall be kept within a concentration range extending from 0.001% to about 3% and including monomeric and polymeric free anhydride glutaric aldehydes having a monomer-polymer ratio of about 3:1 yet excluding unsaturated alpha-beta polymers, the solution to be tamponed with Mg group ions and having a pH above 7 and such an ionic power that the ions are kept in a range of about 250 Å to 300 Å, as spectrophotometrically proven; the solution to have an approximate 0.02% to 3% fixative to be selected out of the Periodic Table's group 8 metal ammoniacal oxychlorates (preferably Fe and Ru), at a temperature higher than 10° C. but less than the degradation temperature of the bath components until a histopathologically controlled satisfactory curing is obtained.

2. Biological material treating process, as claimed in claim 1, characterized by the fact that the animal artery is an internal mammary artery.

3. Biological material treating process, as claimed in claim 2, characterized by the fact that the internal mammary artery is swine's.

4. Biological material treating process, as claimed in claim 2, characterized by the fact that the internal mammary artery is bovine's.

5. A heterologous arterial biograft comprising an arterial duct made of heterologous biological material, said arterial duct having branches bound together and its integrity preserved so as to retain original elasticity within a 40% to 60% range and wall inner surface homogeneity within a 80% to 95% range, wherein the heterologous biological arterial duct is an animal internal mammary artery.

6. A heterologous arterial biograft according to claim 5, wherein the internal mammary artery is a swine mammary artery.

7. A heterologous arterial biograft according to claim 5, wherein the internal mammary artery is a bovine mammary artery.

* * * * *

UNITED STATES PATENT AND TRADEMARK OFFICE
CERTIFICATE OF CORRECTION

PATENT NO. : 4,671,797

DATED : June 9, 1987

INVENTOR(S) : VRANDECIC PEREDO, Mario O.

It is certified that error appears in the above-identified patent and that said Letters Patent is hereby corrected as shown below:

Title Page, Column 1, Item [19] delete "Vrandecic Pedero" and replace therefor -- Vrandecic Peredo --; and Title Page, Column 1, Item [76] Inventor:

delete "Mario O. Vrandecic Pedero" and replace therefor -- Mario O. Vrandecic Peredo --.

Signed and Sealed this

Twelfth Day of January, 1988

Attest:

DONALD J. QUIGG

Attesting Officer

Commissioner of Patents and Trademarks